US00PP37338P2

(12) United States Plant Patent
Radler

(10) Patent No.: US PP37,338 P2
(45) Date of Patent: Mar. 24, 2026

(54) GRANDIFLORA ROSE PLANT NAMED 'Radtriple'

(50) Latin Name: *Rosa hybrida*
Varietal Denomination: Radtriple

(71) Applicant: The Conard Pyle Company, West Grove, PA (US)

(72) Inventor: William Radler, Greenfield, WI (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 19/329,998

(22) Filed: Sep. 16, 2025

(51) Int. Cl.
*A01H 5/02* (2018.01)

(52) U.S. Cl.
USPC ..... Plt./139

(58) Field of Classification Search
USPC ..... Plt./139
CPC ..... A01H 6/749; A01H 5/02
See application file for complete search history.

(56) References Cited

U.S. PATENT DOCUMENTS

PP21,709 P2 2/2011 Carruth
PP30,142 P2 1/2019 Kordes

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of grandiflora rose plant, referred to by its cultivar name, 'Radtriple', is described. The new plant variety forms in abundance on a substantially continuous basis red-colored blossoms. The growth habit is very bushy and compact. Glossy, medium green foliage is formed. Additionally, the new plant variety is particularly well suited for growing as distinctive ornamentation in the landscape.

1 Drawing Sheet

Latin name of genus and species of plant claimed: *Rosa hybrida.*

Variety denomination: 'Radtriple'.

BACKGROUND OF THE INVENTION

The new variety of Grandiflora rose plant of the present invention was created by controlled breeding in June 2015 in Greenfield, Wisconsin by artificial pollination wherein two parents were crossed which previously had been studied in the hope that they would contribute the desired characteristics. The female parent (i.e., the seed parent) was 'RAD8613' (not patented). The male parent (i.e., the pollen parent) of the new plant variety was 'WEKcobeju' (U.S. Plant Pat. No. 21,709).

The parentage of the new plant variety can be summarized as follows:

'RAD8613' x 'WEKcobeju'

The seeds resulting from the above pollination were sown and small plants were obtained which were physically and biologically different from each other. Selective study resulted in the identification of a single plant of the new variety.

The new plant variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new plant variety are homogeneous, stable, and strictly transmissible by such asexual propagation from one generation to another. Accordingly, the new plant variety undergoes asexual propagation in a true-to-type manner.

SUMMARY OF THE INVENTION

It was found that the new variety of grandiflora rose plant of the present invention possesses the following combination of characteristics:

(a) abundantly and substantially continuously forming red-colored blossoms,
(b) exhibiting a very bushy and compact growth habit, and
(c) forming glossy, medium green foliage.

The new plant variety well meets the needs of the horticultural industry. It can be grown to advantage as distinctive ornamentation in parks, gardens, public areas, and residential landscapes. Accordingly, it is particularly well suited for growing in the landscape.

The new plant variety can be readily distinguished from its ancestors. More specifically, the new plant variety displays red-colored flowers and has a denser growth habit compared to the 'RAD8613' parent (i.e., the seed parent), which displays pale pink-white colored flowers. Additionally, the new plant variety displays red-colored flowers and forms more petals (about 30 to 35 petals per flower) compared to the 'WEKcobeju' parent (i.e., the pollen parent), which displays smoky lavender and rusty red-orange-colored blossoms and forms about 16 to 24 petals per flower. Moreover, the new plant variety can be readily distinguished from non-parental related similar varieties. For example, the new plant variety exhibits a very bushy and compact growth habit, typically provides between 1 and 6 blooms per stem, and exhibits a medium sweet fragrance, compared to 'KORroleotu' (U.S. Plant Pat. No. 30,142) which exhibits a very bushy and upright growth habit, typically provides one bloom per stem, and exhibits a very light sweet scent.

The new plant variety has been named 'Radtriple'.

BRIEF DESCRIPTION OF THE PHOTOGRAPH

The accompanying photograph shows, as nearly true as it is reasonably possible to make the same in a color illustration of this character, a typical specimen of the new plant variety and blossoms of the new plant variety. The illustrated rose plant of the new variety was approximately two years of age and was grown outdoors in a field in Cochranville, Pennsylvania, U.S.A. in June 2023.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designations used herein each represent the closest color observed on the majority of the specified botanical feature. The description is based on a two-year-old specimen of the new plant variety, observed during June, while growing on its own roots in a three-gallon container in Cochranville, Pennsylvania.

Botanical classification: *Rosa hybrida* cultivar 'Radtriple'.

Commercial classification: Grandiflora Rose.

Plant:

*Habit*.—Very bushy and compact.

*Height*.—Approximately 90.0 cm on average from the top of the soil plane when growing in a container.

*Width*.—Approximately 90.0 cm on average.

Branches:

*Stem color*.—Old wood: Green Group 138A with aging streaks of Grey Group 201B. — young stems: Base color of Red-Purple Group 59A with some Green Group 137A coming through.

*Length*.—Main stems: approximately 90.0 cm on average. — secondary stems: approximately 40.0 cm on average.

*Diameter*.—Main stems: approximately 4.0 cm on average. — secondary stems: approximately 1.6 cm on average.

*Texture*.—Smooth.

*Prickles*.—Amount: medium; 5 to 6 prickles per internode on upper portion of plant and 6 to 10 prickles per internode on the main stems of the lower half of plant. — young prickles: length is approximately 4.0 mm on average; width is approximately 2.0 mm on average at point of attachment; and color is Red-Purple Group 59A. — old prickles: length is approximately 1.0 cm on average; width is approximately 8.0 mm on average at point of attachment; and color is Red-Purple Group 59B.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Glossiness of upper side*.—Glossy.

*Texture*.—Upper surface: smooth. — under surface: smooth.

*Venation pattern*.—Reticulate.

*Size*.—Terminal leaflet: length is approximately 4.0 cm on average; width is approximately 3.5 cm on average. — lower leaflets: length is typically 3.0 cm to 3.5 cm; width is typically 1.9 cm to 3.0 cm. — 5-Leaflet leaf: length is approximately 10.5 cm on average; width is approximately 7.5 cm on average.

Foliage:

*Young foliage*.—Upper surface color: Yellow-Green Group 147A with Greyed-Purple Group 187A around the edges with indistinguishable venation. — under surface color: Green Group 137B and Greyed-Purple Group 187A with venation of Greyed-Purple Group 184B.

*Old foliage*.—Upper surface color: Green Group 137A with indistinguishable venation. — under surface color: Green Group 138B with indistinguishable venation.

*Petiole*.—Texture: upper surface is hispidulous; under surface is minutely thorny. — length: approximately 1.5 cm on average. — width: approximately 1.0 mm on average. — upper surface color: Green Group 138A. — under surface color: Green Group 143B.

*Rachis*.—Length: approximately 1.8 cm on average. — width: approximately 1.0 mm on average. — upper surface color: Green Group 137A. — under surface color: Green Group 143A.

*Stipules*.—Length: approximately 2.0 cm on average. — width: approximately 3.0 mm on average. — margin: entire to erose. — upper surface color: Green Group 143A. — lower surface color: Green Group 143A.

Inflorescence:

*Number of flowers*.—About 60 to 65 blooms on average on a plant at once.

*Number of blossoms per stem or in a cluster*.—Typically between 1 and 6 blooms per stem on average.

*Peduncle*.—Color: Green Group 143C and Greyed-Red Group 178A. — diameter: approximately 1.0 mm on average. — length: approximately 7.0 cm on average. — surface texture: hispidulous.

*Sepals*.—Number: 5. — upper surface color and texture: Green Group 143A, hispidulous. — under surface color and texture: Green Group 138A, puberulent. — size: length is approximately 2.2 cm on average; width is approximately 8.0 mm on average. — margin: entire with no visible extensions. — shape: lanceolate. — apex: acute to aristate. — base: truncate as it joins the receptacle.

*Buds*.—Shape: ovoid. — size: length is approximately 2.0 cm on average; width is approximately 1.8 cm on average. — color (when opening): Greyed-Purple Group 185B.

*Flower*.—Form: double, cuplike. — profile: concave as it opens, and then outer petals are convex as the bloom ages and opens further. — shape when viewed from the top: globular at initial opening; more irregularly round as petals reflex. — diameter: typically 8.0 cm to 9.0 cm. — height: approximately 4.0 cm on average. — duration: on the plant approximately 10 to 12 days. — petal color when first and fully opened: inner petals: upper surface is Red-Purple Group N57A with a very small basal spot of Yellow Group 8A; under surface is Red-Purple Group 58B with a very small basal spot of Yellow Group 8A; outer petals: upper surface is Red-Purple Group N57A with a very small basal spot of Yellow Group 8A; under surface is Red-Purple Group 58B with a very small basal spot of Yellow Group 8A. — petal color at end of bloom: upper surface is Red-Purple Group 67A with no distinct basal spot; under surface is Red-Purple Group 67C with no distinct basal spot. — petals reflex one by one: yes.

*Fragrance*.—Medium sweet scent.

*Petal*.—Number: 30 to 35 on average. — drop: good. — length: typically 3.5 cm to 4.0 cm. — width: typically 2.5 cm to 3.5 cm. — overall shape: broadly obovate. — margin: entire. — apex shape: rounded to slightly cuspidate. — base shape: cuneate. — texture: upper surface is smooth; lower surface is smooth.

*Petaloids*.—Number: approximately 4 on average. — length: approximately 2.5 cm on average. — width: approximately 8.0 mm on average. — color: upper and under surfaces are Red-Purple Group 58B with a very small basal spot of Yellow Group 8A. — texture: upper surface is smooth; under surface is smooth. — margin: entire. — shape: obovate. — apex: rounded to slightly cuspidate. — base: cuneate.

*Stamen*.—Number: approximately 104. — anthers: number is approximately 104; color is Yellow-Orange Group 16A; length is approximately 2.0 mm on average; and shape is oval. — filaments: length is approximately 7.0 mm on average and color is Yellow-Orange Group 16A.

*Pistils*.—Arrangement: separate and free. — number: approximately 102.— style: length is approximately 5.0 mm on average and color is Greyed-Yellow Group 160C. — stigma: diameter is approximately 1.0 mm on average; shape is fan shaped; color is Greyed-Yellow Group 160C.

*Receptacle*.—Diameter: approximately 1.0 cm on average. — depth: approximately 1.0 cm on average. — shape: urn shaped. — color: Green Group 143C. — surface texture: smooth.

*Pollen*.—Amount: sparse. — color: Yellow-Orange Group 20A.

*Hips/seed*.—None observed.

Development:

*Vegetation*.—Glossy and medium green.

*Blossoming*.—Abundant and continuous from spring through frost; typically, in bloom outdoors from May to November in Southeastern Pennsylvania.

*Resistance to diseases*.—Excellent resistance to black spot (*Diplocarpon rosae*), powdery mildew (*Podosphaera pannosa*) and rust (*Phragmidium tuberculatum*).

*Hardiness*.—Hardy to USDA Zone 4b.

The new 'Radtriple' plant variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of grandiflora rose plant named 'Radtriple' characterized by the following combination of characteristics:

(a) abundantly and substantially continuously forming red-colored blossoms, (b) exhibiting a very bushy and compact growth habit, and (c) forming glossy, medium green foliage;

substantially as herein shown and described.

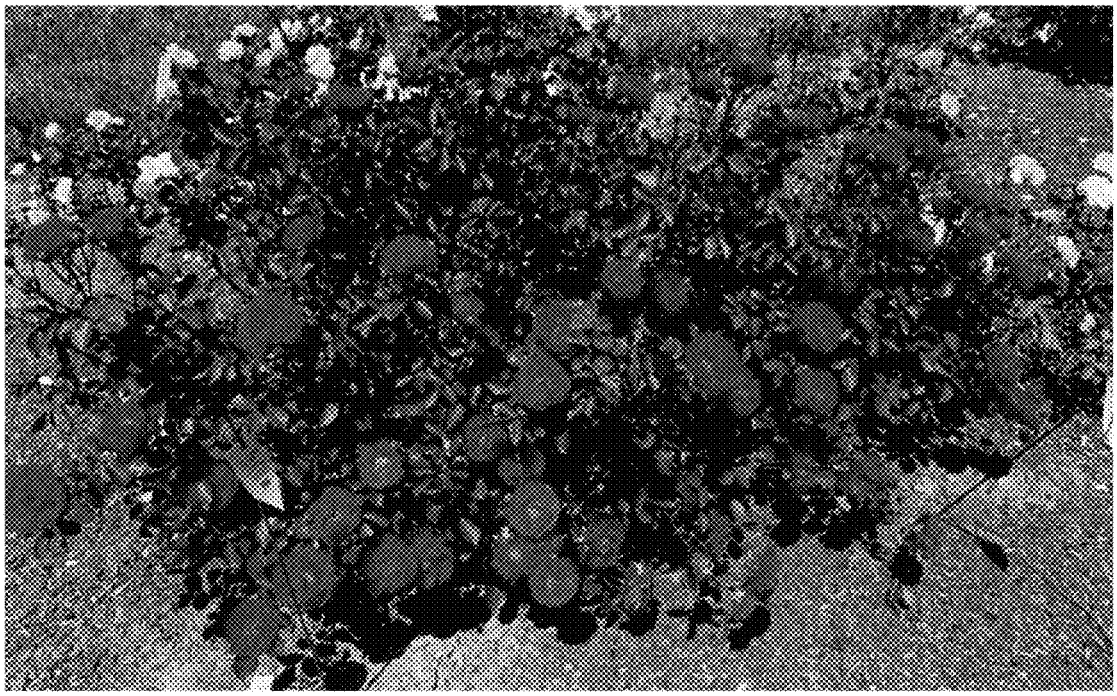

* * * * *